(12) United States Patent
Park et al.

(10) Patent No.: US 8,602,959 B1
(45) Date of Patent: Dec. 10, 2013

(54) METHODS AND DEVICES FOR DELIVERY OF RADIATION TO THE POSTERIOR PORTION OF THE EYE

(76) Inventors: Robert Park, Asheville, NC (US); Luca Brigatti, Rockville, MD (US); Russell J. Hamilton, Tucson, AZ (US)

(*) Notice: Subject to any disclaimer, the term of this patent is extended or adjusted under 35 U.S.C. 154(b) by 242 days.

(21) Appl. No.: 13/111,765

(22) Filed: May 19, 2011

Related U.S. Application Data

(60) Provisional application No. 61/347,233, filed on May 21, 2010.

(51) Int. Cl.
*A61N 5/00* (2006.01)

(52) U.S. Cl.
USPC ..................... 600/3; 600/7; 604/19

(58) Field of Classification Search
USPC ........ 600/3–5, 7; 604/19, 48, 57, 59–60, 200, 604/294, 500, 521
See application file for complete search history.

(56) References Cited

U.S. PATENT DOCUMENTS

| | | | |
|---|---|---|---|
| 2,309,302 A | 1/1943 | Butler et al. | |
| 2,559,793 A | 7/1951 | Pregel | |
| D183,820 S | 10/1958 | Yohe | |
| 3,169,527 A | 2/1965 | Sheridan | |
| 3,662,882 A | 5/1972 | Obermayer | |
| D235,171 S | 5/1975 | Boone | |
| D235,172 S | 5/1975 | Boone | |
| D236,920 S | 9/1975 | Sheridan | |
| 4,248,354 A | 2/1981 | Metzger | |
| 4,300,557 A | 11/1981 | Refojo et al. | |
| D272,089 S | 1/1984 | Glassman | |
| 4,454,151 A * | 6/1984 | Waterbury | ..... 514/413 |
| 4,925,450 A | 5/1990 | Imonti et al. | |
| 4,976,266 A | 12/1990 | Huffman et al. | |
| 5,007,689 A | 4/1991 | Kelly et al. | |
| 5,080,111 A * | 1/1992 | Pallin | ..... 128/898 |
| 5,109,844 A | 5/1992 | de Juan, Jr. et al. | |
| 5,127,831 A | 7/1992 | Bab | |
| 5,167,647 A | 12/1992 | Wijkamp et al. | |
| 5,199,939 A | 4/1993 | Dake et al. | |

(Continued)

FOREIGN PATENT DOCUMENTS

| | | |
|---|---|---|
| AU | 323700 S | 1/2009 |
| AU | 323701 S | 1/2009 |

(Continued)

OTHER PUBLICATIONS

Achar et. al, Principles of Office Anesthesia:Part. I. Infiltrative Anesthesia, Jul. 1, 2002, vol. 66, pp. 91-94.*

(Continued)

*Primary Examiner* — Charles A Marmor, II
*Assistant Examiner* — Laura Fajardo

(57) ABSTRACT

Methods and devices for delivering radiation to a target at a posterior portion of an eye using a brachytherapy-administering device adapted to be inserted into a suprachoroidal space of the eye including a brachytherapy source and a means of advancing the brachytherapy source from a storage position to a radiation position corresponding to a position in a distal portion of the device, positioning the device appropriately such that the distal portion of the device is in close proximity to the target, exposing the target to the brachytherapy source for a predetermined length of time then removing the device and closing incisions made during a surgical procedures to reach the suprachoroidal space of the eye.

8 Claims, 1 Drawing Sheet

(56) References Cited

U.S. PATENT DOCUMENTS

| | | | |
|---|---|---|---|
| D340,111 S | 10/1993 | Yoshikawa | |
| D345,417 S | 3/1994 | Sharipov | |
| D347,473 S | 5/1994 | Nitzsche | |
| 5,364,374 A | 11/1994 | Morrison et al. | |
| 5,392,914 A | 2/1995 | Lemieux et al. | |
| 5,399,298 A | 3/1995 | Kelly et al. | |
| 5,443,505 A * | 8/1995 | Wong et al. | 623/4.1 |
| 5,637,073 A * | 6/1997 | Freire | 600/3 |
| D390,656 S | 2/1998 | Linder | |
| 5,871,481 A | 2/1999 | Kannenberg et al. | |
| 5,893,873 A | 4/1999 | Rader et al. | |
| 5,935,155 A | 8/1999 | Humayun et al. | |
| 5,944,747 A | 8/1999 | Greenberg et al. | |
| 5,947,891 A | 9/1999 | Morrison | |
| 5,970,457 A | 10/1999 | Brant et al. | |
| 6,053,900 A | 4/2000 | Brown et al. | |
| D428,140 S | 7/2000 | Swan | |
| 6,135,984 A | 10/2000 | Dishler | |
| 6,149,643 A | 11/2000 | Herekar et al. | |
| 6,159,205 A | 12/2000 | Herekar et al. | |
| 6,183,410 B1 | 2/2001 | Jacobsen et al. | |
| 6,183,435 B1 | 2/2001 | Bumbalough et al. | |
| 6,278,975 B1 | 8/2001 | Brant et al. | |
| 6,302,839 B1 | 10/2001 | Chernomorsky et al. | |
| 6,402,734 B1 | 6/2002 | Weiss | |
| 6,413,245 B1 | 7/2002 | Yaacobi et al. | |
| 6,443,881 B1 | 9/2002 | Finger | |
| 6,450,938 B1 | 9/2002 | Miller | |
| 6,527,692 B1 | 3/2003 | Weinberger | |
| 6,575,887 B1 | 6/2003 | Schrayer | |
| 6,613,026 B1 | 9/2003 | Palasis et al. | |
| 6,641,518 B2 | 11/2003 | Wolfson et al. | |
| 6,676,590 B1 | 1/2004 | Urick et al. | |
| 6,719,750 B2 | 4/2004 | Varner et al. | |
| 6,749,553 B2 | 6/2004 | Brauckman et al. | |
| 6,755,338 B2 | 6/2004 | Hahnen et al. | |
| D492,778 S | 7/2004 | Narini | |
| 6,800,076 B2 | 10/2004 | Humayun | |
| 6,824,532 B2 | 11/2004 | Gillis et al. | |
| 6,830,174 B2 | 12/2004 | Hillstead et al. | |
| 6,875,165 B2 | 4/2005 | Dejuan, Jr. et al. | |
| 6,918,894 B2 | 7/2005 | Fleury et al. | |
| 6,958,055 B2 | 10/2005 | Donnan et al. | |
| 6,964,653 B2 | 11/2005 | Negron | |
| 6,977,264 B2 | 12/2005 | Fotsch et al. | |
| 7,070,556 B2 | 7/2006 | Anderson et al. | |
| 7,103,416 B2 | 9/2006 | Ok et al. | |
| 7,115,607 B2 | 10/2006 | Fotsch et al. | |
| 7,153,316 B1 | 12/2006 | McDonald | |
| D534,650 S | 1/2007 | Inman et al. | |
| D543,626 S | 5/2007 | Watschke et al. | |
| 7,217,263 B2 | 5/2007 | Humayun et al. | |
| 7,220,225 B2 | 5/2007 | Dejuan, Jr. et al. | |
| 7,223,225 B2 | 5/2007 | DeJuan, Jr. et al. | |
| 7,228,181 B2 | 6/2007 | Greenberg et al. | |
| 7,252,006 B2 | 8/2007 | Tai et al. | |
| 7,273,445 B2 | 9/2007 | Pulido et al. | |
| D553,738 S | 10/2007 | Simpson | |
| 7,276,019 B2 | 10/2007 | DeJuan, Jr. et al. | |
| 7,308,487 B1 | 12/2007 | Dansie et al. | |
| 7,321,796 B2 | 1/2008 | Fink et al. | |
| 7,351,193 B2 | 4/2008 | Foreman et al. | |
| 7,357,770 B1 | 4/2008 | Cutrer et al. | |
| 7,402,155 B2 | 7/2008 | Palasis et al. | |
| D575,396 S | 8/2008 | Wu | |
| 7,485,113 B2 | 2/2009 | Varner et al. | |
| 7,503,474 B2 | 3/2009 | Hillstead et al. | |
| 7,537,593 B2 | 5/2009 | Humayun | |
| 7,547,323 B2 | 6/2009 | Lavigne | |
| 7,560,460 B2 | 7/2009 | Fotsch et al. | |
| 7,563,222 B2 | 7/2009 | Larsen et al. | |
| 7,571,004 B2 | 8/2009 | Roy et al. | |
| 7,579,347 B2 | 8/2009 | Bo et al. | |
| 7,600,533 B2 | 10/2009 | Tai et al. | |
| 7,654,716 B1 | 2/2010 | Bhadri et al. | |
| 7,661,676 B2 | 2/2010 | Smith et al. | |
| 7,684,868 B2 | 3/2010 | Tai et al. | |
| D615,645 S | 5/2010 | Brigatti et al. | |
| D616,087 S | 5/2010 | Brigatti et al. | |
| D616,088 S | 5/2010 | Brigatti et al. | |
| D616,540 S | 5/2010 | Brigatti et al. | |
| 7,729,739 B2 | 6/2010 | Acar et al. | |
| 7,744,520 B2 | 6/2010 | Larsen et al. | |
| 7,774,931 B2 | 8/2010 | Tai et al. | |
| 7,794,437 B2 | 9/2010 | Humayun et al. | |
| 7,803,102 B2 | 9/2010 | Larsen et al. | |
| 7,803,103 B2 | 9/2010 | Hillstead et al. | |
| 7,810,233 B2 | 10/2010 | Krulevitch et al. | |
| 7,827,038 B2 | 11/2010 | Richard et al. | |
| 7,831,309 B1 | 11/2010 | Humayun et al. | |
| 7,842,686 B2 | 11/2010 | Anderson et al. | |
| 7,846,954 B2 | 12/2010 | Zimmermann et al. | |
| 7,879,564 B2 | 2/2011 | Brice et al. | |
| 7,883,717 B2 | 2/2011 | Varner et al. | |
| 7,887,508 B2 | 2/2011 | Meng et al. | |
| D642,266 S | 7/2011 | Marsteller et al. | |
| 2001/0008950 A1 | 7/2001 | Vitali et al. | |
| 2001/0049464 A1 | 12/2001 | Ganz | |
| 2002/0002362 A1 | 1/2002 | Humayun et al. | |
| 2002/0026174 A1 | 2/2002 | Wallace | |
| 2002/0062136 A1 | 5/2002 | Hillstead et al. | |
| 2002/0065448 A1 | 5/2002 | Bradshaw et al. | |
| 2002/0077687 A1 | 6/2002 | Ahn | |
| 2002/0099363 A1 | 7/2002 | Woodward et al. | |
| 2002/0115902 A1 | 8/2002 | Dejuan, Jr. et al. | |
| 2002/0164061 A1 | 11/2002 | Paik et al. | |
| 2002/0198511 A1 | 12/2002 | Varner et al. | |
| 2003/0014306 A1 | 1/2003 | Marko | |
| 2003/0045900 A1 | 3/2003 | Hahnen et al. | |
| 2003/0103945 A1 | 6/2003 | Chen et al. | |
| 2003/0153804 A1 | 8/2003 | Tornes et al. | |
| 2003/0171722 A1 | 9/2003 | Paques et al. | |
| 2003/0184859 A1 | 10/2003 | Liang et al. | |
| 2003/0195201 A1 | 10/2003 | Bo et al. | |
| 2003/0220324 A1 | 11/2003 | Fotsch et al. | |
| 2004/0006067 A1 | 1/2004 | Fotsch et al. | |
| 2004/0039312 A1 | 2/2004 | Hillstead et al. | |
| 2004/0053309 A1 | 3/2004 | Holt et al. | |
| 2004/0133155 A1 | 7/2004 | Varner et al. | |
| 2004/0138515 A1 | 7/2004 | White et al. | |
| 2004/0224777 A1 | 11/2004 | Smith et al. | |
| 2004/0243176 A1 | 12/2004 | Hahnen et al. | |
| 2005/0059956 A1 | 3/2005 | Varner et al. | |
| 2005/0101824 A1 | 5/2005 | Stubbs | |
| 2005/0107824 A1 | 5/2005 | Hillstead et al. | |
| 2005/0148948 A1 | 7/2005 | Caputa | |
| 2005/0149286 A1 | 7/2005 | Acar et al. | |
| 2005/0177019 A1 | 8/2005 | DeJuan, Jr. et al. | |
| 2005/0203331 A1 | 9/2005 | Szapucki et al. | |
| 2005/0227986 A1 | 10/2005 | Bo et al. | |
| 2005/0272931 A1 | 12/2005 | Bo et al. | |
| 2005/0277802 A1 | 12/2005 | Larsen et al. | |
| 2006/0009493 A1 | 1/2006 | Koenig et al. | |
| 2006/0030618 A1 | 2/2006 | Bo et al. | |
| 2006/0052796 A1 | 3/2006 | Perez et al. | |
| 2006/0110428 A1 | 5/2006 | deJuan et al. | |
| 2006/0111605 A1 | 5/2006 | Larsen et al. | |
| 2006/0142629 A1 | 6/2006 | DeJuan, Jr. et al. | |
| 2006/0189838 A1 | 8/2006 | Dejuan, Jr. et al. | |
| 2006/0223026 A1 | 10/2006 | Kuroiwa et al. | |
| 2006/0235877 A1 | 10/2006 | Richard et al. | |
| 2006/0257451 A1 | 11/2006 | Varner et al. | |
| 2006/0287662 A1 | 12/2006 | Berry et al. | |
| 2007/0019790 A1 | 1/2007 | Lewis et al. | |
| 2007/0055089 A1 | 3/2007 | Larsen et al. | |
| 2007/0118010 A1 | 5/2007 | Hillstead et al. | |
| 2007/0179471 A1 | 8/2007 | Christian et al. | |
| 2007/0219546 A1 | 9/2007 | Mody et al. | |
| 2007/0233037 A1 | 10/2007 | Gifford, III et al. | |
| 2007/0248545 A1 | 10/2007 | Brice et al. | |
| 2007/0265248 A1 | 11/2007 | Fotsch et al. | |
| 2007/0265485 A1 | 11/2007 | DeJuan, Jr. et al. | |
| 2008/0027266 A1 | 1/2008 | Lebovic et al. | |
| 2008/0108933 A1 | 5/2008 | Yu et al. | |

(56) References Cited

U.S. PATENT DOCUMENTS

| | | |
|---|---|---|
| 2008/0154204 A1 | 6/2008 | Varner et al. |
| 2008/0161762 A1 | 7/2008 | Stehr et al. |
| 2008/0172086 A1 | 7/2008 | Hillstead et al. |
| 2008/0194649 A1* | 8/2008 | Khatib .................. 514/357 |
| 2008/0200747 A1 | 8/2008 | Wagner et al. |
| 2008/0214887 A1 | 9/2008 | Heanue et al. |
| 2008/0221653 A1 | 9/2008 | Agrawal et al. |
| 2008/0249412 A1 | 10/2008 | Huang et al. |
| 2008/0262512 A1 | 10/2008 | Humayun et al. |
| 2008/0262569 A1 | 10/2008 | Greenberg et al. |
| 2008/0262570 A1 | 10/2008 | Greenberg et al. |
| 2008/0262571 A1 | 10/2008 | Greenberg et al. |
| 2008/0272023 A1 | 11/2008 | McCormick et al. |
| 2008/0281142 A1 | 11/2008 | Lubock et al. |
| 2008/0281254 A1 | 11/2008 | Humayun et al. |
| 2008/0288036 A1 | 11/2008 | Greenberg et al. |
| 2008/0294223 A1 | 11/2008 | Greenberg et al. |
| 2008/0305320 A1 | 12/2008 | Laude et al. |
| 2008/0306611 A1 | 12/2008 | Rowley et al. |
| 2008/0319319 A1 | 12/2008 | Humayun et al. |
| 2009/0016075 A1 | 1/2009 | Bhadri et al. |
| 2009/0030323 A1 | 1/2009 | Fawzi et al. |
| 2009/0036827 A1 | 2/2009 | Cazzini |
| 2009/0069340 A1 | 3/2009 | Balestra et al. |
| 2009/0088784 A1 | 4/2009 | DeBoer et al. |
| 2009/0088843 A1 | 4/2009 | Lu et al. |
| 2009/0101841 A1 | 4/2009 | Boyden et al. |
| 2009/0104960 A1 | 4/2009 | Kelly et al. |
| 2009/0104987 A1 | 4/2009 | Kelly et al. |
| 2009/0112287 A1 | 4/2009 | Greenberg et al. |
| 2009/0131175 A1 | 5/2009 | Kelly et al. |
| 2009/0143124 A1 | 6/2009 | Hughes et al. |
| 2009/0143633 A1 | 6/2009 | Edmundson et al. |
| 2009/0143734 A1 | 6/2009 | Humayun et al. |
| 2009/0146583 A1 | 6/2009 | Bhadri et al. |
| 2009/0149915 A1 | 6/2009 | Greenberg et al. |
| 2009/0177245 A1 | 7/2009 | Ameri et al. |
| 2009/0192493 A1 | 7/2009 | Meng et al. |
| 2009/0227856 A1 | 9/2009 | Russell et al. |
| 2009/0228086 A1 | 9/2009 | Greenberg et al. |
| 2009/0240215 A1 | 9/2009 | Humayun et al. |
| 2009/0264424 A1 | 10/2009 | Bo et al. |
| 2009/0287276 A1 | 11/2009 | Greenberg et al. |
| 2009/0306585 A1 | 12/2009 | Pang et al. |
| 2009/0306594 A1 | 12/2009 | Pang et al. |
| 2009/0306595 A1 | 12/2009 | Shih et al. |
| 2009/0311133 A1 | 12/2009 | Pang et al. |
| 2009/0312742 A1 | 12/2009 | Pang et al. |
| 2010/0004499 A1 | 1/2010 | Brigatti et al. |
| 2010/0004581 A1 | 1/2010 | Brigatti et al. |
| 2010/0004639 A1 | 1/2010 | Pang et al. |
| 2010/0025613 A1 | 2/2010 | Tai et al. |
| 2010/0026957 A1 | 2/2010 | Tanguay, Jr. et al. |
| 2010/0030010 A1 | 2/2010 | Vermeere et al. |
| 2010/0076271 A1 | 3/2010 | Humayun |
| 2010/0100104 A1 | 4/2010 | Yu et al. |
| 2010/0105454 A1 | 4/2010 | Weber et al. |
| 2010/0114039 A1 | 5/2010 | Cazzini |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0131075 A1 | 5/2010 | Ludlow et al. |
| 2010/0157620 A1 | 6/2010 | Bhadri et al. |
| 2010/0168646 A1 | 7/2010 | Greenbaum et al. |
| 2010/0174415 A1 | 7/2010 | Humayun et al. |
| 2010/0197826 A1 | 8/2010 | Agrawal et al. |
| 2010/0228119 A1 | 9/2010 | Brennan et al. |
| 2010/0228123 A1 | 9/2010 | Brennan et al. |
| 2010/0228124 A1 | 9/2010 | Brennan et al. |
| 2010/0228132 A1 | 9/2010 | Brennan et al. |
| 2010/0228238 A1 | 9/2010 | Brennan et al. |
| 2010/0229384 A1 | 9/2010 | Krulevitch et al. |
| 2010/0238288 A1 | 9/2010 | Klaerner et al. |
| 2010/0267647 A1 | 10/2010 | Greenbaum et al. |
| 2010/0268013 A1 | 10/2010 | Larsen et al. |
| 2010/0294041 A1 | 11/2010 | Tai et al. |
| 2010/0305550 A1 | 12/2010 | Meng et al. |
| 2011/0004045 A1 | 1/2011 | Larsen et al. |
| 2011/0021906 A1 | 1/2011 | Hillstead et al. |

FOREIGN PATENT DOCUMENTS

| | | |
|---|---|---|
| AU | 323703 S | 1/2009 |
| AU | 323704 S | 1/2009 |
| WO | 2005016258 A2 | 2/2005 |
| WO | 2007059208 A2 | 5/2007 |

OTHER PUBLICATIONS

Drake et. al, Becker-Shaffer's Diagnosis and Therapy of the Glaucomas, 2009, Mosby Elsevier, 8th Ed. Chapter 34, p. 471.*

J. M. Capping; Radiation scleral necrosis simulating early scleromalacia perforans; Brit. J. Ophthal.; 1973; 57; pp. 425-428.

JC Wen et al; Ocular complications following I-125 brachytherapy for choroidal melanoma; Eye; 2009; 23; 1254-1268.

Messmer E et al.; Histopathologic findings in eyes treated with a ruthenium plaque for uveal melanoma; Graefes Arch Clin Exp Ophthalmol.; 1992; 230 (4): 391-6.

Raghava et al.; Periocular routes for retinal drug delivery, 2004, pp. 99-114, Ashley Publications.

Venkatesh et al.; Comparison of the Efficacy and Safety of Different Methods of Posterior Subtenon Injection; Ocular Immunology and Inflammation; Oct. 1, 2007; pp. 217-223; Infoma Healthcare USA, Inc.

Tenon's Capsule; Fundamentals and Principles; p. 39.

Canavan et al.; Sub-Tenon's administration of local anaesthetic: a review of the technique; 2003; pp. 787-793; British Journal of Anaesthesia.

Dafflon et al.; Posterior sub-Tenon's steriod injections for the treatment of posterior ocular inflammation: indications, efficacy and side effects, Graefe's Arch Clin Exp Ophthalmos, 1999, pp. 289-295; Springer-Verlag 1999.

Tanner et al.; Posterior sub-Tenon's triamcinolone injections in the treatment of uveitis; Royal College of Ophthalmologists; 1998; pp. 679-685.

Thach, MD et al.; A Comparison of Retrobulbar versus Sub-Tenon's Corticosteroid Therapy for Cystoid Macular Edema Refractory to Topical Medications; pp. 2003-2008; Ophthalmology Volue 104, No. 12, Dec. 1997.

Hubbard et al.; A New Ocular Brachytherapy System for the Treatment of Exudative AMD; 2005; Invest Ophthalmo Vis Sci 2005; 46; E-Abstract 2425.

Hubbard, III et al.; A Progress Report on the TheraSight Ocular Brachytherapy Safety and Feasibility Study; 2006; Invest Ophthalmol Vis Sci 2006; 47: E-Abstract 2101.

The Collaborative Ocular Melanoma Study Group; Design and Methods of a Clinical Trial for a Rare Condition: The Collaborative Ocular Melanoma Study; COMS Report No. 3; 1993; Controlled Clinical Trials 14: 362-391; Elsevier Science Publishing Co., Inc.

COMS Coordinating Center; Collaborative Ocular Melanoma Study; Manual of Procedures; Jan. 1995; pp. 1-330; The Wilmer Ophthalmological Institute; The Johns Hopkins School of Medicine (*reduced to cover and Table of Contents due to excessive data [330 pages]).

Hubbard et al.; Cadaver Evaluation of a New Ocular Brachytherapy System; Invest Ophthalmol Vis Sci 2004; 45: E-Abstract 5139.

Golden; SubTenon Injection of Gentamicin for Bacterial Infections of the Eye; pp. S271-S277; The Journal of Infectious Diseases; vol. 124, Supplement; Dec. 1971; University of Chicago.

Snyder, MD, PhD et al.; Antibiotic Therapy for Ocular Infection; Conferences and Reviews; pp. 579-584; WJM, Dec. 1994; vol. 161, No. 6; Therapy for Ocular Infection—Snyder and Glasser.

Baum, M.D. et al.; The Evolution of Antibiotic Therapy for Facterial Conjunctivitis and Keratitis: 1970-2000; pp. 659-672; Cornea, vol. 19, No. 5, 2000; Lippincott Williams & Wilkins, Inc., Philadelphia.

Scoper; Review of Third- and Fourth-Generation Fluoroquinolones in Ophthalmology: In-Vitro and In-Vivo Efficacy; Adv Ther. 2008; 25(10): 979-994; Springer Healthcare Communications.

(56) References Cited

OTHER PUBLICATIONS

Yilmaz, MD et al.; Severe Fungal Keratitis Treated With Subconjunctival Fluconazole; 2003; pp. 454.e1-454.e7; vol. 140, No. 3; Elsevier Inc.

Yilmaz, MD et al.; Severe Fungal Keratitis Treated With Subconjunctival Fluconazole; Apr. 2006; pp. 783-784; vol. 141, No. 4, Correspondence; American Journal of Ophthalmology.

Ikewaki et al.; Peribulbar fungal abscess and endophthalmitis following posterior subtenon injection of triamcinolone acetonide; Diagnolis/Therapy in Ophthalmology; 2008; pp. 102-104; Acta Ophthalmologica; The Authors, Journal compilation, Acta Ophthalmol.

Nayak et al.; Acute orbital abscess complicating deep posterior subtenon triamcinolone injection; Indian Journal of Ophthalmology; vol. 56, No. 3; May-Jun. 2008; downloaded from http://www.ijo.in on Monday, Nov. 2, 2009.

Kusaka et al.; Orbital infection following posterior subtenon triamcinolone injection; 2207; pp. 692-693; Acta Ophthalmologica Scandinavica.

Walker et al.; Conservative management of refractory steroid-induced glaucoma following anterior subtenon steroid injection; 2007; Letters to the Editor; pp. 197-198; The Authors, Journal compilation, Royal Australian and New Zealand College of Ophthalmologists.

Au et al.; Localised abscess following an injection of subtenon triamcinolone acitonide; Correspondence; Eye (2007) 21, 627-674, doi:10.1038/sj.eye.6702671; published online Dec. 15, 2006.

Venkatesh MD, et al.; Posterior subtenon injection of corticosteroids using polytetrafluoroethylene (PEFE) intravenous cannula; Clinical and Experimental Ophthalmology (2002) 30, 55-57; All India Institute of Medical Sciences Campus, India.

Sou-Tung Chiu-Tsao, PH.D., Episcleral Eye Plaques for Treatment of Intraocular Malignancies and Benign Diseases; Chapter 34; pp. 673-705.

Sou-Tung Chiu-Tsao, Ph.D., Pterygium Brachytherapy Physics; Chapter 35; pp. 707-717.

Nath, Ravinder, Ph.D. et al.; Brachytherapy Physics Second Edition; Medical Physics Monograph No. 31; 1013 pages; Medical Physics Publishing; Madison, Wisconsin, USA; 2005.

Jaakkola, Aino; Heikkonen, Jorma; Tarkkanen, Anti and Immonen, Ilkka; Visual function after strontium-90 plaque irradiation in patients with age-related subfoveal choroidal neovascularization; Acta Opthalmologica Scandinavica 1999; 77; pp. 57-61.

Hokkanen, J.; Heikkonen, J.; Holmberg, P.; Theoretical calculations of dose distributions for beta-ray eye applicators; Med. Phys. 24 (2); Feb. 1997 pp. 211-213.

Jaakkola, Aino; Heikkonen, Jorma; Tommila, Petri; Laatikainen, Leila; Immonen, Ilkka; Strontium plaque irradiation of subfoveal neovascular membranes in age-related macular degeneration; Graefe's Arch Clin Exp Ophthalmol (1998); 236; pp. 24-30.

\* cited by examiner

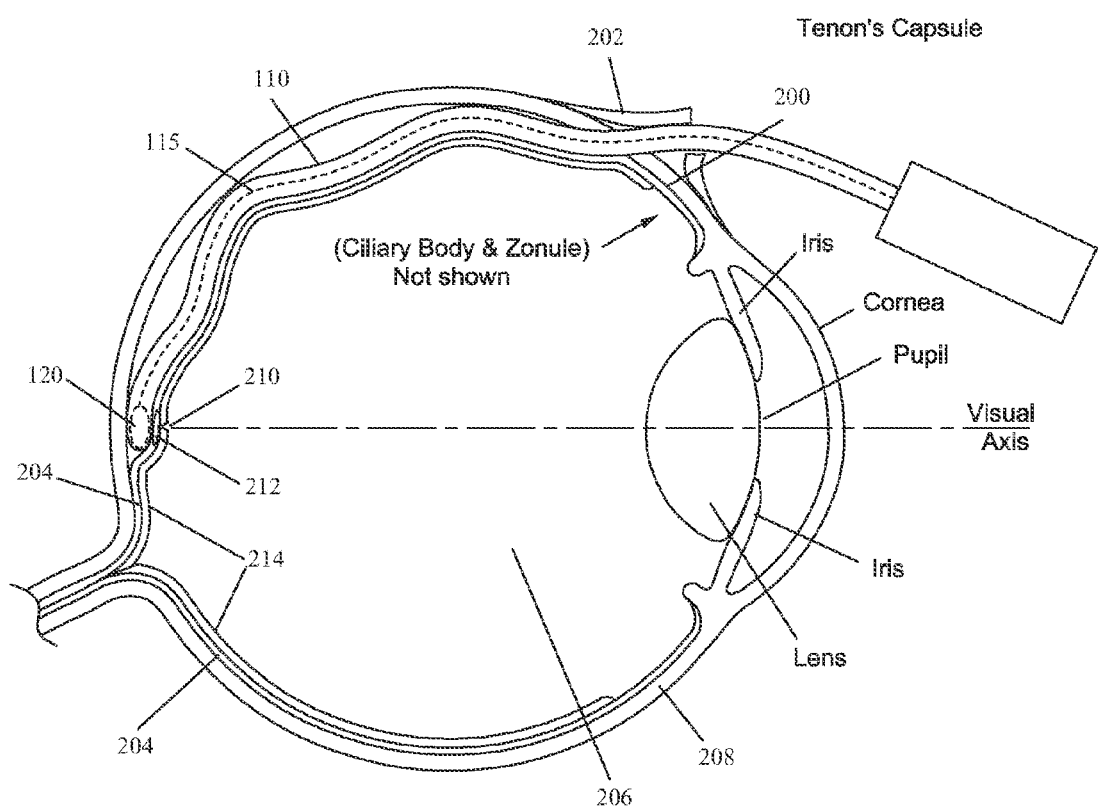

METHODS AND DEVICES FOR DELIVERY OF RADIATION TO THE POSTERIOR PORTION OF THE EYE

CROSS REFERENCE

This application is a non-provisional application which claims priority to U.S. provisional Ser. No. 61/347,233 filed May 21, 2010, the specification of which is incorporated herein by reference in its entirety.

FIELD OF THE INVENTION

The present invention is directed to methods and devices for introducing radiation to the posterior portion of the eye for treating and/or managing eye conditions including but not limited to macula degeneration, more particularly to suprachoroidal methods of introducing radiation to the posterior portion of the eye.

BACKGROUND OF THE INVENTION

Several intraocular diseases and conditions of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, ocular tumors, and glaucoma are several examples.

Age related macular degeneration (ARMD) is the leading cause of blindness in the elderly in the United States. ARMD attacks the center region of the retina 214 (i.e., macula), responsible for detailed vision and damages it, making reading, driving, recognizing faces and other detailed tasks difficult or impossible. Current estimates reveal that approximately forty percent of the population over age 75, and approximately twenty percent of the population over age 60, suffer from some degree of macular degeneration. "Wet" or exudative ARMD (e.g., WAMD) is the type of ARMD that most often causes blindness. In wet ARMD (e.g., WAMD), newly formed choroidal blood vessels (choroidal neovascularization (CNV)) leak fluid and cause progressive damage to the retina. It is estimated that about 15% of all cases of ARMD are of the wet type (WAMD).

Ocular tumors may be primary or secondary. Examples include but are not limited to ciliary body melanomas, choroidal melanomas, hemangiomas, and metastatic tumors. Intraocular tumors can cause blindness or death through direct disruption of tissues or metastatic spread.

Treatment of WAMD has traditionally consisted of thermal laser photocoagulation of the abnormal neovascular membrane. A drawback of laser photocoagulation is that the laser ablates all structures in its path, not just the abnormal vessels but also the normal retina and choroid, resulting in vision loss at the location of laser application. When this treatment is applied to subfoveal membranes (membranes located below the fovea 210, the very center of the macula), the result is an immediate, permanent, severe central vision loss.

More recently, Photodynamic Therapy (PDT) has been applied to subfoveal membranes. In PDT therapy, a photosensitizing (light activated) dye is injected into the patient's bloodstream. A non-thermal (non-burning) laser is applied to the neovascular membrane 212. The dye is activated at the site of the laser application resulting in localized damage to the neovascular membranes. The result is localized damage to the young, abnormal, photosensitized vessels but not the normal vessels and retina tissue. While PDT has yielded better visual results than thermal photocoagulation or observation alone (e.g., no treatment) it does not usually lead to an improvement of vision.

Currently, a standard of practice treatment of WAMD consists of serial intraocular injections of a Vascular Endothelial Growth Factor inhibitor (anti-VEGF), e.g., bevacizumab, ranibizumab, injected directly into the vitreous gel. Anti-VEGF treatment has proven to be the only treatment to date that significantly stabilizes and often improves vision. A drawback of anti-VEGF therapy is a relatively short duration of action, requiring monthly injections. Numerous injections are required with concomitant discomfort and repeated exposure to small but not negligible risks of complications such as infection, inflammation, bleeding, and retinal detachment. A limitation of anti-VEGF treatment is a limited effect of anti-VEGF agents against developed choroidal neovascular membranes (CNVMs). For example, CNVMs are stabilized by anti-VEGF agents, but are not necessarily eliminated. In some cases, cessation of monthly injections of anti-VEGF agents can cause a gradual decline in vision as the CNVMs are reactivated.

Intraocular tumors such as melanomas may be treated with external beam radiation therapy, brachytherapy, and/or with chemotherapy, the goal of the therapies being to selectively damage reproducing cells. External beam radiation therapy disrupts the reproducing cells (e.g., tumor cells) and can cause regression of the tumor. However, the high-energy radiation used with external beam radiation therapy has the potential risk to induce radiation retinopathy, which may cause long-term retinal vascular damage and/or decreased vision. Chemotherapy may be applied via systemic administration of through injections into ocular tissues.

Brachytherapy is treatment of a region by placing radioactive isotopes in, on, or near it. Compared to external beam radiation therapy, brachytherapy uses a small, less powerful radiation source placed in close proximity to the tumor, which limits the radiation exposure to surrounding tissues. The Collaborative Ocular Melanoma Study (COMS), a multicenter randomized trial sponsored by the National Eye Institute and the National Cancer Institute, demonstrated the utility of brachytherapy for the treatment of ocular cancers and/or tumors. The technique employs an invasive surgical procedure to allow placement of a surface applicator (called an episcleral plaque) that is applied extraocularly by suturing it to the sclera 208. The gold plaque contains an inner mold into which radioactive iodine 125 (I-125) seeds are inserted. The gold plaque serves to shield the tissues external to the eye while exposing the sclera, choroid, choroidal melanoma, and overlying retina to radiation. The plaque remains fixed for a few days to one week in order to deliver approximately 85 Gy to the tumor apex.

Currently under investigation, brachytherapy treatments for WAMD generally involve performing a pars plana vitrectomy to remove most of the vitreous gel and placing a cannulum containing the radioactive seed 120 in direct contact with the retina overlying the neovascular membrane (NVM). A pars plana vitrectomy presents risks associated with manipulation of the vitreous and placement of a probe on the retinal surface. Risks associated with the procedure include endophthalmitis, retinal detachment, cataract formation, bleeding, glaucoma and mechanical retinal damage (from direct contact) and those of general anesthesia, often required for this type of surgery.

The present invention features methods and devices for delivery of radiation to the posterior portion of the eye (e.g., for WAMD, for ocular tumors, etc.) via a suprachoroidal procedure. A brachytherapy source (e.g., a radioactive seed)

is placed in close proximity to a choroidal neovascular membrane (CNVM) via the suprachoroidal space (between the choroid and sclera).

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description.

BRIEF DESCRIPTION OF THE DRAWINGS

FIG. 1 is a cross sectional view of an example of a cannula 110 of the present invention inserted according to the methods of the present invention. Briefly, the method comprises inserting a cannula through the conjunctiva 202, Tenon's capsule 200, and sclera. The cannula remains outside of the choroid 204 and retina.

DESCRIPTION OF PREFERRED EMBODIMENTS

The present invention features methods and devices for delivery of radiation to the posterior portion of the eye via a suprachoroidal procedure. Without wishing to limit the present invention to any theory or mechanism, it is believed that the suprachoroidal method of delivering radiation to the posterior portion of the eye of the present invention is advantageous (e.g., over an intravitreal procedure) for several reasons. For example, the suprachoroidal procedure is less invasive than an intravitreal procedure and does not require extensive surgical dissections (e.g., it does not violate the vitreous cavity 206, does not require a preliminary vitrectomy). Thus, this unique procedure is faster, easier, and will present fewer side effects and/or complications than other methods that otherwise require dissections. Moreover, the suprachoroidal method may allow for simpler surgical procedures (e.g., local anesthesia as opposed to general anesthesia) with faster recovery times. Depot medication (e.g., chemotherapy) can be administered simultaneously very close to the target tissue, CNVM, tumor, etc.

The present invention is not limited to treatment of age-related macular degeneration or ocular tumors but may include retinal vascular diseases such as proliferative diabetic retinopathy and glaucoma (e.g., ciliary body ablation via suprachoroidal brachytherapy).

The suprachoroidal methods of the present invention allow for other structures (e.g., sclera) to help guide and hold the device in place when in use. Keeping the brachytherapy-administering device (e.g., cannula, microcatheter) in a fixed location and at a distance from the target during the treatment reduces the likelihood of errors and increases the predictability of dose delivery. In an intravitreal approach (e.g., irradiating the target area by directing the radiation from within the vitreous chamber from anteriorly to the retina of the eye back towards the target), a physician is required to hold the device in a fixed location and a fixed distance from the target in the spacious vitreous chamber. It may be difficult for the physician to hold precisely that position for any length of time. Furthermore, it is generally not possible for the physician/surgeon to know the exact distance between the probe and the retina; he/she can only estimate the distance.

Novel Suprachoroidal Brachytherapy

The present invention features a method of introducing radiation to the posterior portion of the eye for treating disease and conditions including but not limited to WAMD and ocular tumors via a suprachoroidal procedure. The method comprises obtaining a brachytherapy-administering device (e.g., a cannula, a microcatheter, etc.) adapted to place a brachytherapy source (e.g., a radioactive seed) disposed therein in close proximity to a target, e.g., a choroidal neovascular membrane (CNVM), macula, retina, sclera, choroid, neovascular growth, etc., via the suprachoroidal space (between the choroid and sclera). Entering the suprachoroidal space does not require a pars plana vitrectomy, removal of the vitreous, or manipulation of the retina. The brachytherapy-administering device comprises a means of advancing the brachytherapy source from a storage position to a radiation position, the radiation position corresponding to a position in a distal portion of the device configured to appropriately irradiate the target.

The method further comprises performing surgical procedures to reach the suprachoroidal space (see Example 1 below) and inserting the brachytherapy-administering device into the suprachoroidal space such that the distal portion of the device is in close proximity to the target. The physician then appropriately positions the device (e.g., via gross positioning methods and fine positioning methods.). The method further comprises advancing the brachytherapy source through the device from the storage position (e.g., in a shielded portion) to the distal portion (e.g., tip) via the advancing means. The method further comprises exposing the target to the radiation of the brachytherapy source for a predetermined length of time and subsequently removing the device from the suprachoroidal space. The method further comprises closing incisions made during the surgical procedures (e.g., scleral incisions, conjunctiva incisions). As used herein, a brachytherapy source that is placed "in close proximity" means that the brachytherapy source is about 0 mm to about 10 mm from the target.

In some embodiments, the brachytherapy source (e.g., radioactive seed) irradiates the target and the target receives a dose rate of greater than about 10 Gy/min. In some embodiments, the brachytherapy source (e.g., radioactive seed) provides a dose rate of greater than about 11 Gy/min to the target. In some embodiments, the brachytherapy source (e.g., radioactive seed) provides a dose rate of greater than about 12 Gy/min to the target. In some embodiments, the brachytherapy source (e.g., radioactive seed) provides a dose rate of greater than about 13 Gy/min to the target. In some embodiments, the brachytherapy source (e.g., radioactive seed) provides a dose rate of greater than about 14 Gy/min to the target. In some embodiments, the brachytherapy source (e.g., radioactive seed) provides a dose rate of greater than about 15 Gy/min to the target.

In some embodiments, the brachytherapy source (e.g., radioactive seed) provides a dose rate between about 10 to 15 Gy/min. In some embodiments, the brachytherapy source (e.g., radioactive seed) provides a dose rate between about 15 to 20 Gy/min. In some embodiments, the brachytherapy source (e.g., radioactive seed) provides a dose rate between about 20 to 30 Gy/min. In some embodiments, the brachytherapy source (e.g., radioactive seed) provides a dose rate between about 30 to 40 Gy/min. In some embodiments, the brachytherapy source (e.g., radioactive seed) provides a dose rate between about 40 to 50 Gy/min. In some embodiments, the brachytherapy source (e.g., radioactive seed) provides a dose rate between about 50 to 60 Gy/min. In some embodiments, the brachytherapy source (e.g., radioactive seed) provides a dose rate between about 60 to 70 Gy/min. In some embodiments, the brachytherapy source (e.g., radioactive seed) provides a dose rate between about 70 to 80 Gy/min. In some embodiments, the brachytherapy source (e.g., radioactive seed) provides a dose rate between about 80 to 90 Gy/min. In some embodiments, the brachytherapy source (e.g., radioactive seed) provides a dose rate between about 90 to 100 Gy/min. In some embodiments, the brachytherapy source (e.g., radioactive seed) provides a dose rate of greater than 100 Gy/min.

In some embodiments, the brachytherapy source (e.g., radioactive seed) provides a dose rate between about 15 to 20 Gy/min to the target. In some embodiments, the brachytherapy source (e.g., radioactive seed) provides a dose rate between about 20 to 25 Gy/min to the target. In some embodiments, the brachytherapy source (e.g., radioactive seed) provides a dose rate between about 25 to 30 Gy/min to the target. In some embodiments, the brachytherapy source (e.g., radioactive seed) provides a dose rate between about 30 to 35 Gy/min to the target. In some embodiments, the brachytherapy source (e.g., radioactive seed) provides a dose rate between about 35 to 40 Gy/min to the target. In some embodiments, the brachytherapy source (e.g., radioactive seed) provides a dose rate between about 40 to 50 Gy/min to the target. In some embodiments, the brachytherapy source (e.g., radioactive seed) provides a dose rate between about 50 to 60 Gy/min to the target. In some embodiments, the brachytherapy source (e.g., radioactive seed) provides a dose rate between about 60 to 70 Gy/min to the target. In some embodiments, the brachytherapy source (e.g., radioactive seed) provides a dose rate between about 70 to 80 Gy/min to the target. In some embodiments, the brachytherapy source (e.g., radioactive seed) provides a dose rate between about 80 to 90 Gy/min to the target. In some embodiments, the brachytherapy source (e.g., radioactive seed) provides a dose rate between about 90 to 100 Gy/min to the target. In some embodiments, the brachytherapy source (e.g., radioactive seed) provides a dose rate greater than about 100 Gy/min to the target.

In some embodiments, the area exposed to the radiation is about 0.1 mm to about 0.5 mm in diameter. In some embodiments, the area exposed to the radiation is about 0.5 mm to about 2 mm in diameter. In some embodiments, the area exposed to the radiation is about 2 mm to 3 mm in diameter. In some embodiments, the area exposed to the radiation is about 3 mm to 5 mm in diameter. In some embodiments, the area exposed to the radiation is about 5 mm to 10 mm in diameter. In some embodiments, the area exposed to the radiation is about 10 mm to 25 mm in diameter.

In addition to brachytherapy, the methods of the present invention (e.g., suprachoroidal procedure) may be used for delivering drugs immediately after, before, or concomitantly with irradiation (e.g., localized chemotherapy combined with brachytherapy). Permanent or biodegradable printed tapes or microspheres with radiation sources or medications may be considered for temporary or permanent implantation. The procedure may be performed under local anesthesia, which may help avoid complications associated with general anesthesia and/or pars plana vitrectomy procedures.

Brachytherapy-Administering Device

The present invention also features brachytherapy-administering devices for delivering a brachytherapy source (e.g., radioactive seed) via a suprachoroidal procedure. In some embodiments, the device is a cannula, a micro-catheter, or an endoscope-like device, however the device is not limited to these configurations. The brachytherapy-administering device is adapted to be inserted into a suprachoroidal space of the eye and to position the brachytherapy source (e.g. radioactive seed) in close proximity to a target.

The disclosures of the following U.S. Patents are incorporated in their entirety by reference herein: U.S. Patent Application No. 2010/0004499; U.S. Patent Application No. 2010/0004581.

In some embodiments, the device comprises a generally cylindrical, shielded handle that houses the brachytherapy source (e.g., radioactive seed), e.g., in the storage position. The device may further comprise a generally hollow cannula (e.g., 18-30 gauge) connected to the handle. The cannula comprises a proximal portion (attached to the handle) and a distal portion. The device further comprises an advancing means for advancing the brachytherapy source (e.g., radioactive seed) from the storage position (e.g., in the handle) through the cannula to a radiation position (e.g., the tip of the distal portion).

The cannula may be generally curved so as to contour the eye. The tip may be generally rounded to ease advancement of the distal portion to the posterior pole of the eye (to the target) via the suprachoroidal space.

In some embodiments, the device further comprises a light (e.g. fiber optic light), for example disposed in the distal portion at or near the tip. The light may function to help the physician during the fine positioning of the device in the suprachoroidal space. In some embodiments, the cannula is generally flexible.

In some embodiments, the advancing means comprises a flexible wire 115 to which the brachytherapy source (e.g., radioactive seed) is connected. For example, when the advancing means is activated, the wire may push the seed from the storage position to the radiation position, and then ultimately the advancing means may be used to return the brachytherapy source to the storage position after use. The advancing means is not limited to a wire mechanism. For example, the advancing means may include but is not limited to a plunger mechanism, a pneumatic mechanism (e.g., air pressure, vacuum), a hydrostatic pressure mechanism, the like, or a combination thereof.

In some embodiments, the tip of the distal portion may be closed, or in some embodiments, the tip may be open (e.g., an open bore cannula) for deposition of the tape, medication, or microspheres.

In some embodiments, the device comprises a locator, for example a physical mark (e.g., a visible mark and/or a physical protrusion) disposed on the device. In some embodiments, the locator is for aligning the device to facilitate the positioning of the distal portion and/or tip and/or brachytherapy source (e.g., radioactive seed).

EXAMPLE 1

Example of a Surgical Procedure

The following example describes a surgical procedure utilizing methods of the present invention. The present invention is not limited to this example.

Preparation

The eye being operated is dilated, e.g., by instillation of tropicamide and epinephrine. The patient is brought to the operating room where cardiac monitoring and an intravenous line are established. A retrobulbar injection of a mixture of xilocaine and marcaine is given. Standard ophthalmic prepping and draping is performed, and a lid speculum is placed.

Incisions

A conjunctival incision is performed at the superotemporal quadrant about 3-4 mm posterior to the limbus, followed by an incision in the underlying Tenon's capsule to expose bare sclera. A bipolar cautery is used to cauterize episcleral vessels and render a vascular a patch of scleral bed. An initial, partial thickness scleral incision is performed followed by a series of shallower incisions to deepen the initial one. The incisions are repeated until the dark purple uveal tissue is visualized, indicating that the sclera has been penetrated fully and the suprachoroidal space has been reached.

Brachytherapy

The distal portion of a brachytherapy-administering device (e.g., a cannula or microcatheter, e.g., a curved cannula or microcatheter, e.g., a curved cannula or microcatheter with a fiber optic light at its tip) is inserted in the suprachoroidal space and advanced posteriorly by a predetermined amount until the macula region is reached (gross positioning). The surgeon then adjusts the position of the tip and places it directly below the CNVM or tumor by observing the light via transillumination through choroid and sclera with the aid of an indirect ophthalmoscope (fine positioning). The surgeon (or an assistant) operates the advancing mechanism of the brachytherapy-administering device and advances the brachytherapy source (e.g., radioactive seed) from the shielded handle of the device to the tip (distal portion) of the device. The brachytherapy source (e.g., radioactive seed) is left in place for a predetermined amount of time (e.g., around two minutes). When the treatment is completed the brachytherapy source (e.g., radioactive seed) is retracted in the shielded handle, the device is removed from the eye, and the instrument placed in a shielded container.

Closure

The scleral incision is then closed with one suture. The conjunctiva incision is then closed with one or more sutures and antibiotics are administered through a subconjunctival injection.

Disposition

An antibiotic ointment is then placed in the eye and a protective shield is placed on the eye. The patient is then escorted in the post-operative area and discharged after a short period of observation with instruction to return the following day for follow-up.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the invention.

What is claimed is:

1. A method of delivering radiation to a target at a posterior portion of an eye, said method comprising:
 (a) obtaining a brachytherapy-administering device adapted to be threaded through a suprachoroidal space of the eye, the device comprising a brachytherapy source and a means of advancing the brachytherapy source from a storage position to a radiation position, the radiation position corresponding to a position in a distal portion of the device;
 (b) performing surgical procedures at an incision site to reach the suprachoroidal space of the eye;
 (c) inserting the brachytherapy-administering device into the suprachoroidal space and threading the device appropriately through the suprachoroidal space wherein the device glides between the sclera and choroid tissue such that the distal portion of the device is in close proximity to the target, the target being a distance from the incision site;
 (d) advancing the brachytherapy source from the storage position to the radiation position;
 (e) exposing the target to the brachytherapy source for a predetermined length of time;
 (f) removing the brachytherapy-administering device from the suprachoroidal space; and
 (g) closing incisions made during the surgical procedures to reach the suprachoroidal space of the eye.

2. The method of claim 1, wherein the surgical procedures to reach the suprachoroidal space of the eye include dilating the eye.

3. The method of claim 1, wherein the surgical procedures to reach the suprachoroidal space of the eye include performing a retrobulbar injection of a mixture of xilocaine and marcaine.

4. The method of claim 1, wherein the surgical procedures to reach the suprachoroidal space of the eye include performing a conjunctival incision at a superotemporal quadrant about 3-4 mm posterior to a limbus, and performing an incision in a Tenon's capsule to expose bare sclera.

5. The method of claim 4 further comprising cauterizing episcleral vessels.

6. The method of claim 1, wherein the surgical procedures to reach the suprachoroidal space of the eye include performing an initial, partial thickness scleral incision and performing a series of shallower incisions to deepen the initial, partial thickness scleral incision.

7. The method of claim 1, wherein the incisions made during the surgical procedures to reach the suprachoroidal space of the eye include a scleral incision and a conjunctival incision.

8. The method of claim 1 further comprising administering antibiotics through a subconjunctival injection.

* * * * *